United States Patent [19]

Nadelson

[11] 4,016,170

[45] Apr. 5, 1977

[54] OXADIAZOLYL BENZAMIDES

[75] Inventor: Jeffrey Nadelson, Lake Parsippany, N.J.

[73] Assignee: Sandoz, Inc., E. Hanover, N.J.

[22] Filed: Nov. 18, 1975

[21] Appl. No.: 633,014

Related U.S. Application Data

[63] Continuation-in-part of Ser. No. 599,851, July 28, 1975, abandoned.

[52] U.S. Cl. .................. 260/307 G; 260/247.2 A; 260/293.65; 424/272
[51] Int. Cl.$^2$ ...................................... C07D 271/06
[58] Field of Search ... 260/307 G, 293.65, 247.2 A

[56] References Cited

UNITED STATES PATENTS 3,471,509  10/1969  McKillip ................. 260/307 G

*Primary Examiner*—Donald G. Daus
*Assistant Examiner*—D. B. Springer
*Attorney, Agent, or Firm*—Gerald D. Sharkin; Robert S. Honor; Timothy G. Rothwell

[57] ABSTRACT

Substituted or unsubstituted oxadiazolyl benzamides, e.g., o-(3-phenyl-1,2,4-oxadiazol-5-yl)-N-methyl-benzamide, are prepared by reacting a corresponding substituted or unsubstituted oxadiazoyl benzoic acid alkyl ester with an amine and are useful as minor tranquilizers and sleep inducers.

6 Claims, No Drawings

OXADIAZOLYL BENZAMIDES

This application is a continuation-in-part of copending application Ser. No. 599,851 filed July 28, 1975, now abandoned.

This invention relates to oxadiazolyl benzamides which exhibit minor tranquilizer and sleep inducer activity. More particularly, it relates to substituted or unsubstituted oxadiazolyl benzamides, intermediates thereof and to processes for their preparation.

The compounds of this invention may be represented by the following structural formula:

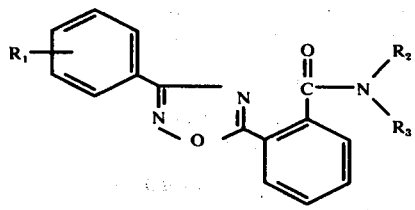

(I)

where $R_1$ represents hydrogen, fluoro, lower alkyl, i.e. alkyl having 1 to 4 carbon atoms, e.g. methyl, ethyl, isopropyl and the like, lower alkoxy, i.e. alkoxy having 1 to 4 carbon atoms, methoxy, alkoxy, isopropoxy and the like, or trifluoromethyl, and $R_2$ and $R_3$ each independently represent hydrogen or lower alkyl as defined above, and $R_2$ and $R_3$ together with N represent

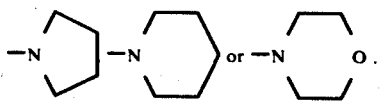

The compounds of formula (I) are prepared according to the following reaction scheme:

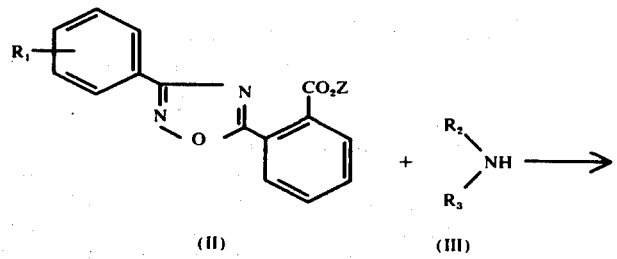

(II)

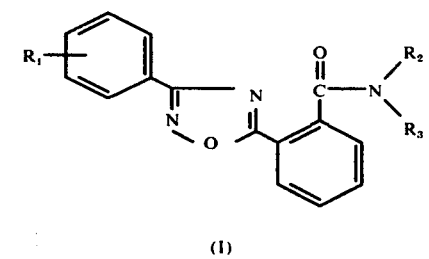

(I)

where

Z represents lower alkyl as defined above, and $R_1$, $R_2$ and $R_3$ are as defined above.

The compounds of formula (I) are prepared by treating a compound of the formula (II) with a compound of the formula (III) in the presence of an inert solvent. The reaction may be run in a single phase system using an anhydrous amine of formula (III) in the presence of an aromatic hydrocarbon such as benzene, toluene, and the like or a lower alkanol such as methanol, ethanol and the like. The reaction, however, is preferably run in a two phase system in the presence of a mixture of water and a water-immiscible solvent. Although the particular immiscible solvent is not critical, aromatic hydrocarbons such as benzene, toluene and the like, ethers such as tetrahydrofuran, diethyl ether and the like, and methylene chloride, are preferred, in particular water in combination with diethylether. The temperature of the reaction is not critical, but it is preferred that the reaction be carried out at a temperature between about 0° to 100° C., preferably at room temperature. The reaction may be run from 12 to 30 hours, preferably from about 16 to 24 hours. The product is removed using conventional techniques, e.g. trituration followed by filtration.

The compounds of formula (II) are prepared according to the following reaction scheme:

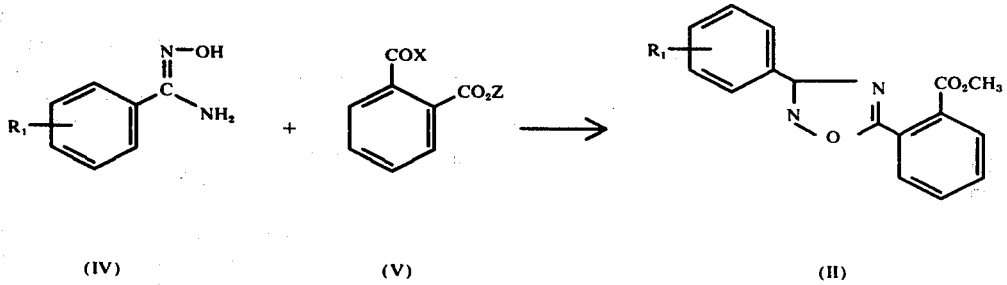

(IV)　　(V)　　(II)

where

X represents halo having an atomic weight of about 19 to 36, and $R_1$ and Z are as defined above.

The compounds of formula (II) are prepared by reacting a compound of the formula (IV) with a compound of the formula (V) in a non-aqueous medium employing a catalyst, for example, a strong Lewis acid or a strong mineral acid. If a Lewis acid is employed, it is preferably stannic tetrachloride, ferric chloride, alummium chloride, boron trifluoride, or especially boron trifluoride etherate. If a mineral acid is used, it is preferably concentrated sulfuric acid, phosphoric acid, polyphosphoric and the like, preferably concentrated sulfuric acid. When using a Lewis acid, the reaction may be carried out in the presence of an inert solvent such as tetrahydrofuran, diethylether, dioxane and the like, or carbon tetrachloride, nitrobenzene and the like, preferably dioxane. A solvent is not required when a strong mineral acid is employed, but solvents such as those employed for the Lewis acid may be utilized. The temperature of the reaction is not critical, but it is preferred that the reaction be carried out a a temperature between about 50° to 150° C., preferably from about 75° to 105° C. The reaction may be run from about 10 to 30 hours, preferably from about 16 to 24 hours. The product is removed using conventional techniques, e.g., evaporation.

Many of the compounds of formulae (III), (IV) and (V) are known and may be prepared by methods described in the literature. The compounds of formulae (III), (IV) and (V) not specifically described may be prepared by analogous methods from known starting materials.

The compounds of formula (I) are useful because they possess pharmacological activity. In particular, the compounds are useful as central nervous system depressants, especially as sleep inducers and minor tranquilizers, as indicated by (1) their ability to produce docility in behavior tests in mice given 25 to 200 mg/kg of animal body weight, i.p. of the test compound according to the 30-word adjective check sheet system basically as described by Irwin S. Gordon (Research Conference, Medicinal Chemistry, 1959) and Chen (Symposium on Sedative and Hypnotic Drugs, Williams and Wilkins, 1954); (2) by their ability to antagonize chronic convulsions and death in mice given 33 to 125 mg/kg i.p. of N-sulfamoylazepine; (3) by the hexobarbital reinduction method of Winter, (J. Pharmacol and Exp. Therap., 94, 7–11, 1948) in which the reinduction of anesthesia after recovery from hexobarbital induces anesthesia is used to determine sedative-hypnotic activity in mice given 70 mg/kg of animal body weight, i.p. of hexobarbital followed immediately after the mice regain their righting reflexes by 25 to 200 mg/kg of animal body weight, i.p. of the test compound; and (4) by scoring for loss of righting reflex according to the method of Reed-Muench (American Journal of Hygiene, 27:493–497, 1938) in which mice are administered 12.5 mg/kg i.p. thioridazine, immediately after which test compound is administered at dosages of 5 to 100 mg/kg in a volume of 0.1 ml/10 g. body weight. Thirty minutes after dosing, the mice are scored for loss of righting reflex.

For such usage, the compounds may be administered orally or parenterally as such or admixed with conventional pharmaceutical carriers.

The dosage of active ingredient employed for minor tranquilizer use may vary depending on the severity of the condition being treated. However, in general, satisfactory results are obtained when a compound of formula (I) is administered at a daily dosage of from about 2 milligrams to about 150 milligrams per kilogram of animal body weight p.o., preferably given in divided doses 2 to 4 times a day, or in sustained release form. For most larger mammals (e.g., primates), the total daily dosage is from about 150 milligrams to about 1000 milligrams. Dosage forms suitable for internal use comprise from about 35 to about 500 milligrams of active compound in intimate admixture with a solid or liquid pharmaceutically acceptable carrier or diluent.

The dosage of active ingredient employed for sleep inducer use may vary depending on the severity of the condition being treated. However, in general, satisfactory results are obtained when a compound of the formula (I) is administered at a daily dosage of from about 2 milligrams to about 100 milligrams per kilogram of animal body weight p.o., typically given in a single dose at bedtime. For most larger mammals, the total daily dosage is from about 150 milligrams to about 1000 milligrams, preferably at bedtime in a single dose, and dosage forms suitable for internal administration comprise from about 35 to about 500 milligrams of the compound in admixture with a solid or liquid pharmaceutical carrier or diluent. The preferred pharmaceutical compositions from the standpoint of preparation and ease of administration are solid compositions, particularly hardfilled capsules and tablets.

EXAMPLE 1 o-(3-phenyl-1,2,4-oxadiazol-5-yl)-benzoic acid methyl ester

A solution of 13.6 g. (0.1 mole) benzamide oxime in 625 milliliters dioxane is treated dropwise with 19.8 g. (0.1 mole) 2-chloroformyl benzoic acid methyl ester in 200 milliliters dioxane. This mixture is then refluxed for one hour, cooled slightly and treated with 3.3 milliliters of boron trifluoride etherate. The reaction mixture is refluxed for 18 hours. The resulting residue is cooled and filtered to remove a small amount of solid. The filtrate is evaporated in vacuo and the resulting oil is dissolved in ether, washed with water, 10 percent sodium carbonate, water and then brine. The ether solution is dried over anhydrous magnesium sulfate decolorized with charcoal filtered to remove the charcoal and the filtrate evaporated in vacuo to give o-(3-phenyl-1,2,4-oxadiazol-5-yl)-benzoic acid methyl ester.

Following the above procedure and using in place of benzamide oxime an equivalent amount of:
 a. p-fluoro-benzamide oxime,
 b. p-methyl-benzamide oxime,
 c. p-methoxy-benzamide oxime, or
 d. m-trifluoromethyl-benzamide oxime,
there is obtained
 a. o-(3-[p-fluorophenyl]-1,2,4-oxadiazol-5-yl) benzoic acid methyl ester,
 b. o-(3-[p-tolyl]-1,2,4-oxadiazol-5-yl)-benzoic acid methyl ester,
 c. o-(3-[p-anisyl]-1,2,4-oxadiazol-5-yl)-benzoic acid methyl ester, or
 d. o-(3-[m-trifluoromthylphenyl]-1,2,4-oxadiazol-5-yl)-benzoic acid methyl ester, respectively.

EXAMPLE 2 o-(3-phenyl-1,2,4-oxadiazol-5-yl)-N-methyl benzamide

A solution of 6.16 g. (0.022 mole) o-(3-phenyl-1,2,4-oxadiazol-5-yl)-benzoic acid methyl ester in 150 milliliters ether is treated with 150 milliliters 40 percent methyl amine in water. The resulting two-phase system is stirred vigorously for 19 hours. The ether is evaporated, and the resulting mixture extracted with methylene chloride. The organic phase is washed with water and then brine, dried over anhydrous magnesium sulfate, filtered, and evaporated in vacuo. The resulting solid is triturated with ether and filtered to give o-(3-phenyl-1,2,4-oxadiazol-5-yl)-N-methyl benzamide, m.p. 145°–146° C.

Following the above procedure and using in place of methyl amine, an equivalent amount of:
a. concentrated ammonium hydroxide solution,
b. isopropyl amine,
c. pyrrolidine,
d. piperidine, or
e. morpholine,
there is obtained
a. o-(3-phenyl-1,2,4-oxadiazol-5-yl)-benzamide,
b. o-(3-phenyl-1,2,4-oxadiazol-5-yl)-N-isopropyl benzamide,
c. o-(3-phenyl-1,2,4-oxadiazol-5-yl)-1-benzoylpyrrolidine,
d. o-(3-phenyl-1,2,4-oxadiazol-5-yl)-1-benzoylpiperidine, or
e. o(3-phenyl-1,2,4-oxadiazol-5-yl)-4-benzoylmorpholine, respectively.

The o-(3-phenyl-1,2,4-oxadiazol-5-yl)-N-methylbenzamide of this Example is an effective sleep inducer when orally administered to an animal in need of said treatment at a dosage of 200 milligrams just before bedtime. The o-(3-phenyl-1,2,4-oxadiazol-5-yl)-N-methylbenzamide of this Example is also an effective minor tranquilizer when orally administered to an animal in need of said treatment at a dosage of 100 milligrams 2 to 4 times per day.

EXAMPLE 3

Following the procedure of Example 2, and using in place of o-(3-phenyl-1,2,4-oxadiazol-5-yl)-benzoic acid methyl ester an equivalent amount of
a. o-(3-[p-fluorophenyl]-1,2,4-oxadiazol-5-yl)-benzoic acid methyl ester,
b. o-(3-[p-tolyl]-1,2,4-oxadiazol-5-yl)-benzoic acid methyl ester,
c. o-(3-[p-anisyl]-1,2,4-oxadiazol-5-yl)-benzoic acid methyl ester, or
d. o-(3-[m-trifluoromethylphenyl]-1,2,4-oxadiazol-5-yl)-benzoic acid methyl ester
there is obtained
a. o-(3-[p-fluorophenyl]-1,2,4-oxadiazol-5-yl)-N-methyl benzamide,
o-(3-[p-tolyl]-1,2,4-oxadiazol-5-yl)-N-methyl benzamide,
c. o-(3-[p-anisyl]-1,2,4-oxadiazol-5-yl)-N-methyl benzamide, or
d. o-(3-[m-trifluoromethylphenyl]-1,2,4-oxadiazol-5-yl)-N-methyl benzamide, respectively.

What is claimed is:
1. A compound of the formula:

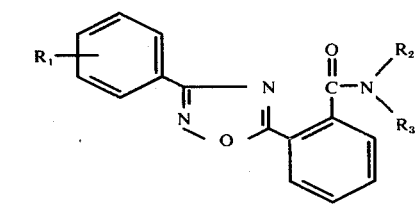

where
$R_1$ represents hydrogen, fluoro, lower alkyl having 1 to 4 carbon atoms, lower alkoxy having 1 to 4 carbon atoms, or trifluoromethyl, and
$R_2$ and $R_3$ each independently represents hydrogen or lower alkyl as defined above, and
$R_2$ and $R_3$ together with N represent

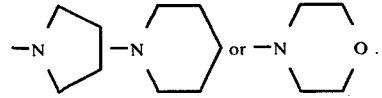

2. A compound of the formula:

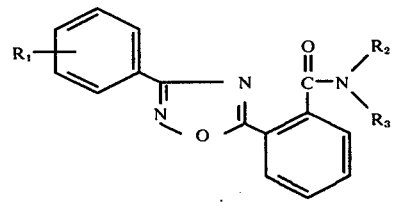

where
$R_1$ represents hydrogen and
$R_2$ and $R_3$ each independently represents hydrogen or lower alkyl having 1 to 4 carbon atoms.

3. A compound of the formula:

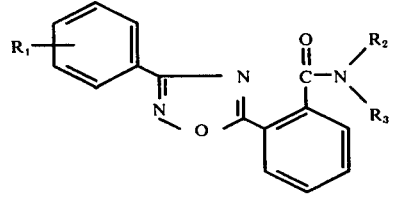

where
$R_2$ and $R_3$ are as defined in claim 1.

4. A compound of the formula:

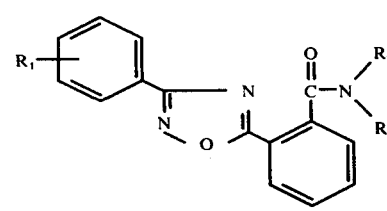

where
$R_1$ is fluoro and
$R_2$ and $R_3$ are as defined in claim 1.

5. A compound of the formula:

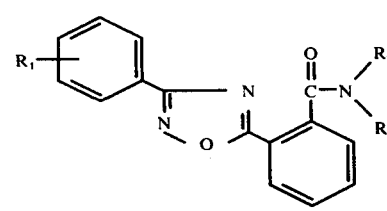

where
$R_2$ and $R_3$ each independently represents hydrogen or lower alkyl having 1 to 4 carbon atoms, and
$R_1$ is as defined in claim 1.

6. The compound of claim 2 which is o-(3-phenyl-1,2,4-oxadiazol-5-yl)-N-methylbenzamide.

* * * * *